(12) United States Patent
Crompvoets et al.

(10) Patent No.: US 8,594,787 B2
(45) Date of Patent: Nov. 26, 2013

(54) SYNCHRONISING A HEART RATE PARAMETER OF MULTIPLE USERS

(75) Inventors: Floris Maria Hermansz Crompvoets, Eindhoven (NL); Martin Ouwerkerk, Eindhoven (NL); Willem Franke Pasveer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 387 days.

(21) Appl. No.: 12/991,162

(22) PCT Filed: Apr. 24, 2009

(86) PCT No.: PCT/IB2009/051690
§ 371 (c)(1),
(2), (4) Date: Nov. 5, 2010

(87) PCT Pub. No.: WO2009/136307
PCT Pub. Date: Nov. 12, 2009

(65) Prior Publication Data
US 2011/0066205 A1   Mar. 17, 2011

(30) Foreign Application Priority Data
May 9, 2008   (EP) .................................. 08155934

(51) Int. Cl.
*A61N 1/08* (2006.01)
(52) U.S. Cl.
USPC .............................................. 607/17; 607/18
(58) Field of Classification Search
USPC ...................................... 607/17, 18
See application file for complete search history.

(56) References Cited

U.S. PATENT DOCUMENTS

| 6,208,894 | B1 * | 3/2001 | Schulman et al. ................. 607/2 |
| 6,358,201 | B1 | 3/2002 | Childre et al. |
| 2004/0082976 | A1 * | 4/2004 | Kalgren et al. .................. 607/32 |
| 2004/0225203 | A1 * | 11/2004 | Jemison et al. ............... 600/300 |
| 2005/0007884 | A1 | 1/2005 | Lorenzato |
| 2005/0209503 | A1 * | 9/2005 | Elliott ............................. 600/26 |
| 2006/0061468 | A1 * | 3/2006 | Ruha ........................ 340/539.12 |
| 2007/0270668 | A1 | 11/2007 | Childre et al. |
| 2007/0299354 | A1 | 12/2007 | Striepe et al. |

FOREIGN PATENT DOCUMENTS

| JP | 59232380 A | 12/1984 |
| WO | 2007057032 A1 | 5/2007 |

\* cited by examiner

*Primary Examiner* — Christopher D Koharski
*Assistant Examiner* — Natasha Patel

(57) ABSTRACT

A method of synchronizing a heart rate parameter of multiple users includes generating a pacing signal at a specific frequency, measuring a physiological parameter of each of the multiple users, presenting to each user an output based upon the measured physiological parameter of the respective user, and presenting to each user an output based upon the generated pacing signal. The measured physiological parameter could include heart rate variability. In one embodiment, the step of presenting to each user an output based upon the generated pacing signal, include presenting a first user with a first output, and presenting a second user with a second output, where the second output is out of phase with the first output.

16 Claims, 10 Drawing Sheets

SYNCHRONISING A HEART RATE PARAMETER OF MULTIPLE USERS

FIELD OF THE INVENTION

This invention relates to a method of, and system for, synchronizing a heart rate parameter of multiple users.

BACKGROUND OF THE INVENTION

It is well known that respiration modulates the heart rate (respiratory sinus arrhythmia, RSA). Meditation techniques such as yoga make use of this principle. The variation in heart rate or heart rate variability (HRV) is attributed to the autonomous nervous system (ANS). An increase in heart rate is attributed to the parasympathic (vagal) nervous system while a decrease in heart rate is attributed to the sympathetic nervous system. In meditation techniques (such as practiced in Zen Buddhism) the low frequency part of the spectrum of the heart rate variability is increased with respect to the high frequency part of the spectrum. This is regarded as beneficial (relaxing) for the well-being of the individual that is practicing the meditation.

In order to assist individuals, it is known to provide output to a user. For example, United States of America Patent Application Publication US 2005/0209503 discloses a method of presenting audible and visual cues for synchronizing the breathing cycle with an external timing reference for purposes of synchronizing the heart rate variability cycle with the breathing cycle. The method of presenting audible and visual cues thereby helps a user achieve coherence of the heart rate variability cycle. A family of audible and visual indicators is specified for purposes of communicating breathing phase, change of breathing phase, progression of time within a phase, and progression of the phase relative to the internal perception of the practitioner.

This technology and other existing applications such as Heartmath (available on the World Wide Web at heartmath.com) and Resperate (available on the World Wide Web at Resperate.com) are all focused on a single user.

SUMMARY OF THE INVENTION

It is therefore an object of the invention to improve upon the known art.

According to a first aspect of the present invention, there is provided a method of synchronizing a heart rate parameter of multiple users comprising generating a pacing signal at a specific frequency, measuring a physiological parameter of each of the multiple users, presenting to each user an output based upon the measured physiological parameter of the respective user, and presenting to each user an output based upon the generated pacing signal.

According to a second aspect of the present invention, there is provided a system for synchronizing a heart rate parameter of multiple users comprising a processor arranged to generate a pacing signal at a specific frequency, and, for each user, a sensor arranged to measure a physiological parameter of a user, and an output system arranged to present to the user an output based upon the measured physiological parameter of the respective user, and to present to the user an output based upon the generated pacing signal.

Owing to the invention, it is possible to provide a synchronization system that is applicable to multiple individuals. In this system there is proposed an application which measures and considers the benefit of synchronized heart beat variability for two (or more) persons. This has many different applications, for example in meditations techniques such as tantra. For example, tantra teaches that contrary breathing leads in two individuals leads to a higher ecstasy level, and this can be achieved using the system of the present invention. In one embodiment, the measured physiological parameter comprises heart rate variability (HRV). Direct feedback to the users, which may be visual, of HRV provides a quicker way of determining whether a HRV measurement (interbeat interval) falls within a coherence range (within certain distance of circle bounding box). In the known systems, for example such as Heartmath, for instance, uses power spectrum analysis of HRV which is rather slow (one minute) and sensitive to sudden short events.

In this embodiment, the system provides for the synchronizing of heart beats between different persons. Heart rate variability of multiple persons is measured and analyzed using a time based method, Heart rate coherence is monitored using interbeat interval ellipses (which can be represented in a two-dimensional visual output). Breaks of the coherence state due to, for instance distraction or startle, result in an abrupt and immediate deviation from the ellipsoidal path, which will be shown the visual feedback, This allows fast visualization and detection of sudden events while maintaining guidance and a measure of coherence for the user. Additionally, when simultaneously the motion of the heart rate sensor is monitored, the events due to motion artifacts can be filtered out of the data flow the digital domain.

Ideally, the step of presenting to each user an output based upon the measured physiological parameter of the respective user comprises displaying a helicoidal representation of the user's heart rate variability over time. The use of a helix provides a display to each user that can show the information about variability over time in a way that is easily accessible to the users.

Preferably, the step of presenting to each user an output based upon the generated pacing signal, comprises presenting a first user with a first output, and presenting a second user with a second output, the second output out of phase with the first output. The system can be used to synchronize the heart rate parameter (such as heart speed and/or variability) of two (or more) people, but not necessarily so that they are in phase. The frequency of tine pacing signal that is used control the users' hearts is the same for both (or all) users, but is not necessarily in the same phase.

The system could be operated to achieve a 180 degrees phase shift in the heart rates of the participants. In a system using a (large) group of users, the female members can have a heart rate variability/respiration rhythm phase 180 degrees shifted from the male members. In this case it is necessary for the system to determine the gender of each user, via a user input or by accessing a user's profile. The system can be operated to achieve, in principle, any desired phase shift.

Advantageously, the step of generating a pacing signal at a specific frequency comprises using at least one of the measured physiological parameters as an input into the generation of the pacing signal. The signal that is used to drive the synchronization between the users can be derived (in whole or in part) from the output of one or more of the users. For example, if several users are detected as being already in relatively close synchronization, this can be used as the basis for the generation of the pacing signal. This is an efficient method of generating the pacing signal.

Ideally, the methodology further comprises presenting to a user an output based upon the measured physiological parameter of a different user. In addition to their own feedback, a user can also be provided with feedback relating to a different user. For example, in a system that has two users, then the output to each user could show the current performance of both of the users, which may be superimposed on each other. This supports a greater provision of information to the users, which in turn greatly improves the speed and accuracy of the synchronization efforts of the users.

In a second embodiment, the system can provide synchronized coherent group meditation or interpersonal contact enhancement service, which may be Internet based. A synchronized pacer breathing pacer can facilitate the attunement of people joining in a group meditation. Being part of an attuned group can be a transformative experience. If such an attunement is offered through the internet much larger audiences can be in tune with each other, greatly strengthening the beneficial effect. The effect of large groups of people in attunement is under study by the global consciousness project of Princeton University.

BRIEF DESCRIPTION OF THE DRAWINGS

Embodiments of the present invention will now be described, by way of example only, with reference to the accompanying drawings, in which:—

DETAILED DESCRIPTION OF THE EMBODIMENTS

Figure 1:
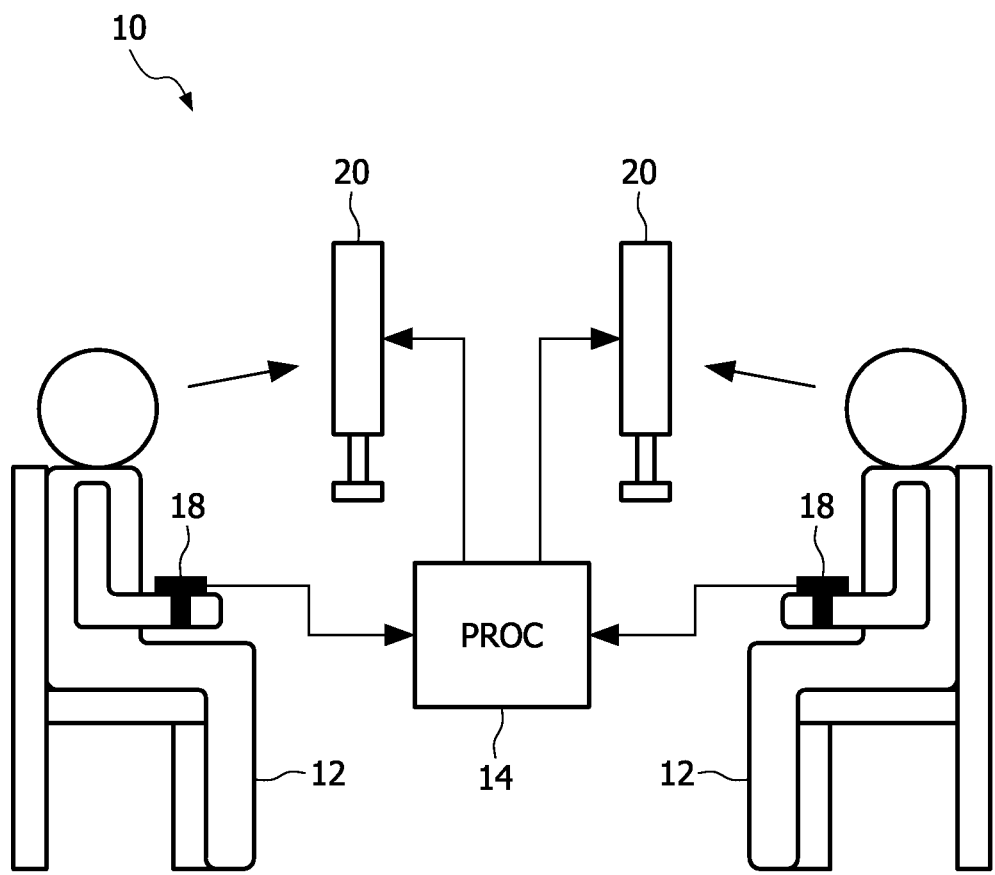
FIG. 1 is a schematic diagram of a system for synchronizing a heart rate parameter of multiple users.
Figure 1:
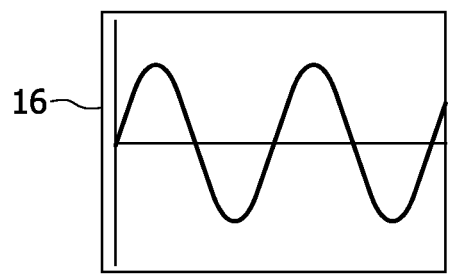

A first embodiment of a system 10 for synchronizing a heart rate parameter of multiple users 12 is shown in FIG. 1, in this example a heart rate parameter of two users is being synchronized. In this Figure, the two users 12 are shown as being at the same physical location, but this need not be the case. The two users 12 could be located remotely from one another and be connected by a wide area network such as the Internet. The users 12 need not be connected directly to one another; they could both be connected to a web service provided by a website, for example.

The system 10 also comprises a processor 14, which is arranged to generate a pacing signal 16 at a specific frequency, and, for each user 12, a sensor 18, that is arranged to measure a physiological parameter of the respective user 12, and an output system 20 (here a display device) arranged to present to the respective user an output based upon the measured physiological parameter of the user 12, and to present to the user an output based upon the generated pacing signal 16. The actual output to the users 12 is discussed in more detail below with respect to FIGS. 3 to 10.

In FIG. 1, each user 12 is shown wearing a sensor 18 fastened to their wrist, to measure their heart rate. In a practical implementation of the system 10, there is no requirement that both users 12 use the same sensor 18, or even that the same physiological parameter is being measured for each user 12. For example, a first user 12 could be using a sensor 18 that measures a galvanic skin response, and a second user 12 could be using a sensor 18 that consists of a camera that is monitoring the user's breathing. Multiple sensors 18 could be used for an individual user 12, in order to either measure multiple physiological parameters, or to obtain a more accurate measurement of the specific physiological parameter. The measured physiological parameter could comprise heart rate variability.

The step of presenting to each user 12 an output based upon the generated pacing signal 16, comprises presenting a first user 12 with a first output, and presenting a second user 12 with a second output, the second output out of phase with the first output. The synchronization that is desired between the two users 12 need not be an in-phase synchronization. For example, it may be desired to synchronies the heart rate parameter of the two users 12 such that they are out of phase, for example by 180 degrees.

In general, the compliance with the breathing pacing can be measured with a 3D accelerometer incorporated in a heart rate sensor, provided the heart rate sensor is worn on the torso (chest or abdomen), such as with a belt. Such a 3D accelerometer can be incorporated using, for example the Analog Devices ADXL330. Deviations from compliance can then be signaled to the user 12. For meditations it is advantageous to be motionless and the spine needs to be truly vertical. The level of restlessness as well as the spinal orientation can also be derived from the accelerometer output.

Figure 2:
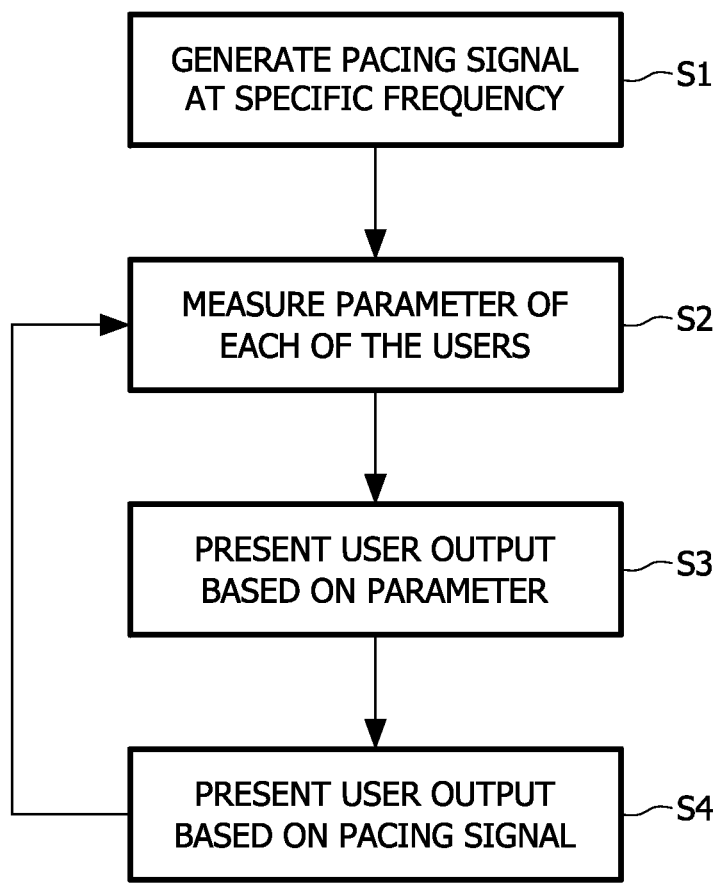
FIG. 2 is a flowchart of a method of operating the system of FIG. 1.

FIG. 2 summarizes the method of operating the system of FIG. 1. The method of synchronizing the heart rate parameter of multiple users comprises, at step S1, the step of generating the pacing signal 16 at the specific frequency. This is followed at step S3, by the measuring of the physiological parameter of each of the multiple users 12. Once the parameters have been measured, then this is followed by step S3, of presenting to each user 12 an output based upon the measured physiological parameter of the respective user 12, and step S4, of presenting to each user 12 an output based upon the generated pacing signal 16. A loop is shown in the flowchart, as the physiological parameters of each of the multiple users 12 will be continually measured and the feedback of step S3 will respond in a like wise manner.

The step S1 of generating the pacing signal 16 at a specific frequency can comprise using at least one of the measured physiological parameters as an input into the generation of the pacing signal 16. In this case step S2 either occurs before or concurrently with step S1. The pacing signal 16 can be based upon the current state of one of the users 12. For example, the two users 12 may be using the system 10 to train themselves to have their heart rates 180 degrees out of phase. The system 10 may measure the current heart rate of the users and determine which of those measured rates is to be used as the basis for the pacing signal 16, for example using the lower measured rate as the frequency of the pacing signal 16.

Step S3 may also be augmented by further presenting to a user 12 an output based upon the measured physiological parameter of a different user 12. Therefore, in addition to seeing their own current performance, a user 12 may see the performance of one or more other users.

A more complex system than that shown in FIG. 1 may be based around the measurement of heart rate variability (HRV). In this embodiment, the essential features of the system 10 include the measuring of HRV from multiple persons 12 using the system 10 (for instance using the C2+ made by J&J Engineering, Poulsbo, Wash., USA), and syncing the HRV from the multiple persons 12 with each other using a stimulus (visual, audible, touch).

The stimulus is based upon pacing signal 16, and the frequency of the pacing signal 16 is the same for each person. As mentioned above, the phase of this pacing signal 16 can be set differently for each person 12. The actual phase of the measured HRV of multiple persons 12 is recovered and checked whether it corresponds to the dictated phase of the pacing signal 16, by the processor 14. In a preferred embodiment, the HRV signal measured by the sensors 18 is processed in interbeat intervals (time domain) by the processor 14.

Although the feedback provided to the user can be visual, audible, or tactile for example, in the preferred embodiment of the system 10, the HRV Time series is plotted in two dimensions on a display device: t-t_n vs. t-t_(n−i), where t_n is the nth measured interbeat interval and where i is an integer. This provides feedback on phase difference between the HRV signals and hence respiration pattern from both persons 12.

Figure 3:
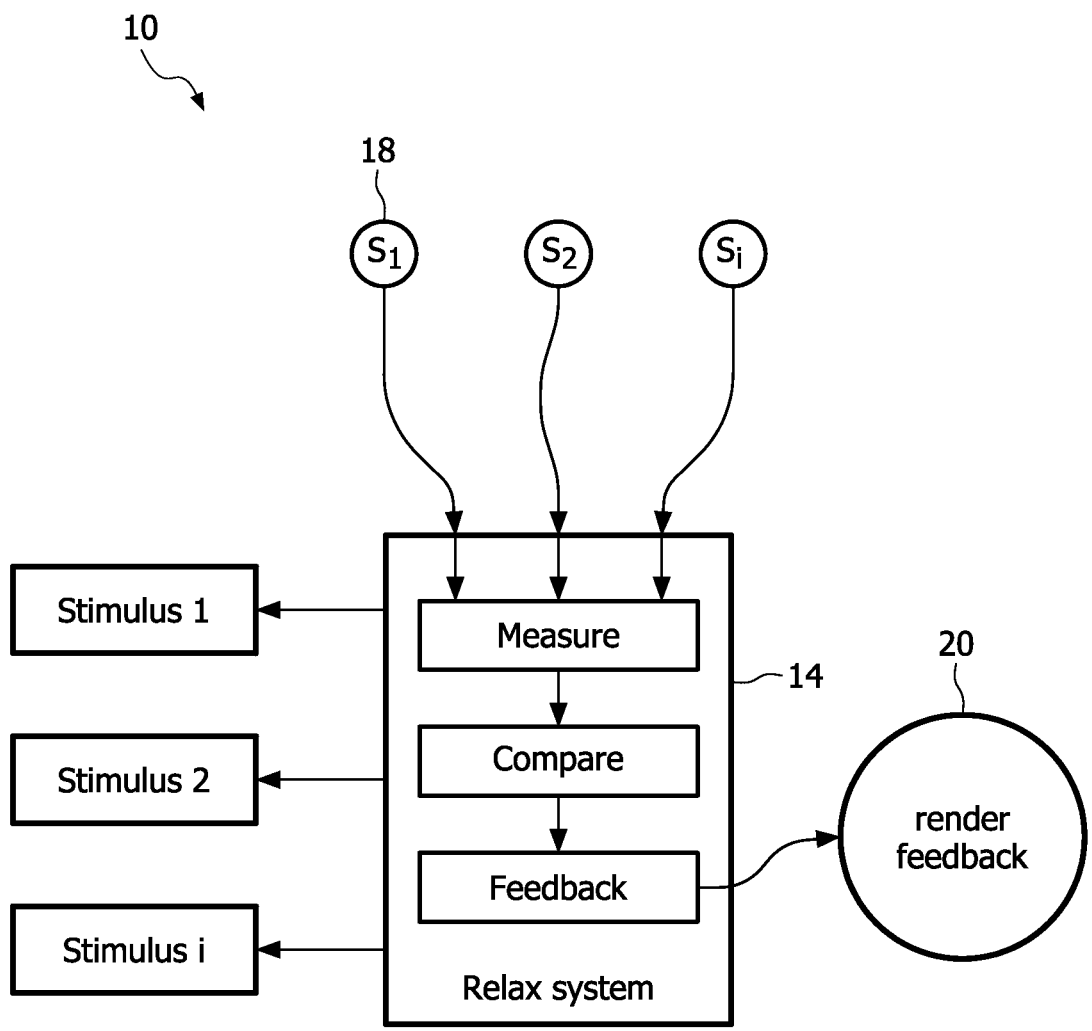
FIG. 3 is a schematic diagram of a second embodiment of the system.

An overview of the system of this embodiment of the invention is depicted in FIG. 3 which shows an overview of this embodiment of the system 10. The relax system 10 measures, compares and gives feedback on the HRV signals acquired by the system 10 via a number of sensors 18 labeled $S_j$ to $S_j$. Each sensor 18 measures the heart beat (HRV) of one person 12. Examples of sensors 18 that can detect heart beat and HRV are a photoplethysmograph, an ECG recorder, and a device for measuring a ballistocardiogram. The system 10 can provide a breathing pacer stimulus for each person 12 separately.

Figure 4:
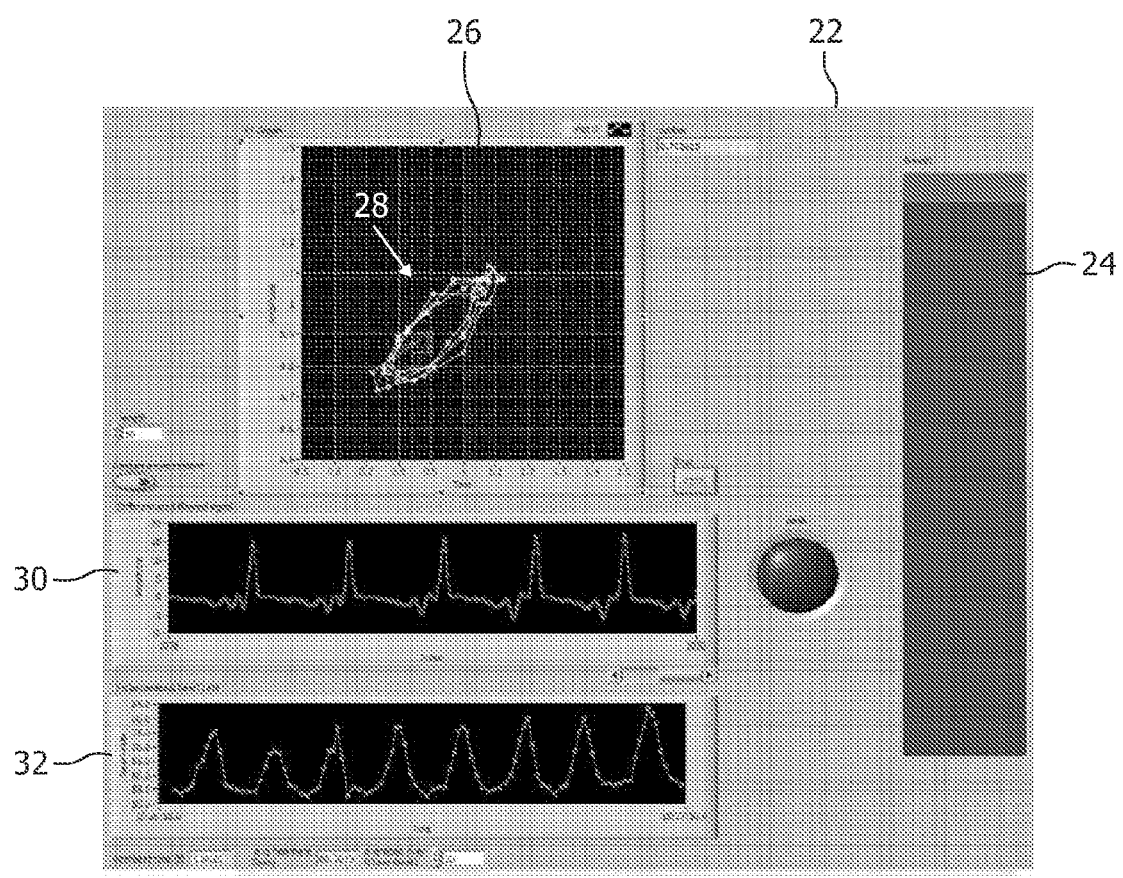
FIGS. 4 to 6 show different views of a graphical interface for use in the system of FIG. 3.

FIG. 4 shows a graphical interface 22 of a computer program run by the processor 14, which has the functionality of the system 10, as described with respect to FIG. 3. The computer program provides a visual breathing pacer stimulus 24 (the bar 24 on the right in FIG. 4). When the bar 24 goes up one person 12 inhales while the other person exhales 12 (two stimuli effectively using one visual pacer). The bar 24 is the output 24 based upon the generated pacing signal 16. The movement of the bar 24 is designed to control the breathing (and thereby the heart rate) of the user 12 that is using the system 10. It is assumed that both users are viewing the same bar 24, but individual bars 24 can be used to provide the feedback to the users 12.

FIG. 4 is a screen-dump of computer implemented application. On the right is shown the breathing pacer, as an oscillating bar 24. The upper graph 26 shows the IBI ellipses 28 of two persons in two different colors. These ellipses 28 are the outputs 28 based upon the measured physiological parameters of the users 12. The middle graph 30 shows the heart beat over time of one user 12. The lower graph 32 shows the heart rate variability of this user 12 over time. The heart rate data is acquired in this embodiment with a photoplethysmograph. The middle graph 30 visualizes the heart beat pulses of one person. The lower graph 32 depicts the heart rate variability (HRV) of the same person. From the HRV the interbeat interval IBI [in seconds] is determined.

Figure 5:
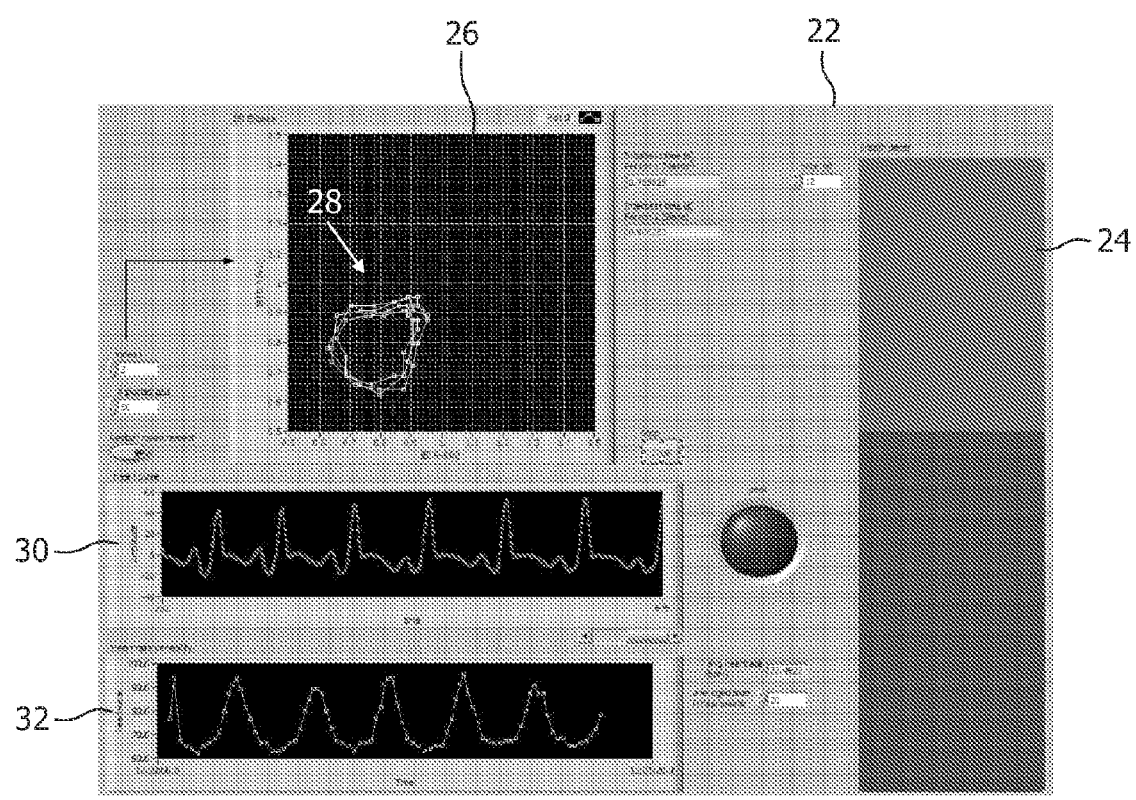

The program run by the processor also acquires the IBI data of a second user 12. The upper graph 26 visualizes the IBI data of both users 12. Different colors are used, and in this example, a white ellipse represents the IBI data of a first user 12 while a (smaller) red ellipse represents the IBI data of a second user 12. The nth measured IBI is plotted on the x-axis versus the n+ith measured IBI on the y-axis. This results in the ellipses 28 as shown in the graph 26 (i=1). For i=0 the plot will be a straight line through the origin. In order to get a circular plot it is necessary to plot IBI n vs. IBI n+$i_{circle}$. Here, $i_{circle}$ is estimated in the following way:

$$i_{circle} = \left[ \frac{T_{pacer}}{IBI_{average}} \right] / 4$$

where $T_{pacer}$ is the period of the pacer in seconds and $IBI_{average}$ is the average IBI in seconds. The ratio $T_{pacer}/IBI_{average}$ is the number of datapoints for one pass of the ellipse. Dividing this number by 4 as shown in the equation above gives the 90 degrees phase factor to turn the ellipse into a circle. For each person the $i_{circle}$ can be different, but in practice they do not differ too much (less than a factor 2). An example of a circular plot is shown in FIG. 5. Here i=3 (closest integer value) yields the best approximation to a circular plot. FIG. 5 shows the ellipse transformed to a circle using an index of i=3 using the formula for $i_{circle}$.

Figure 6:
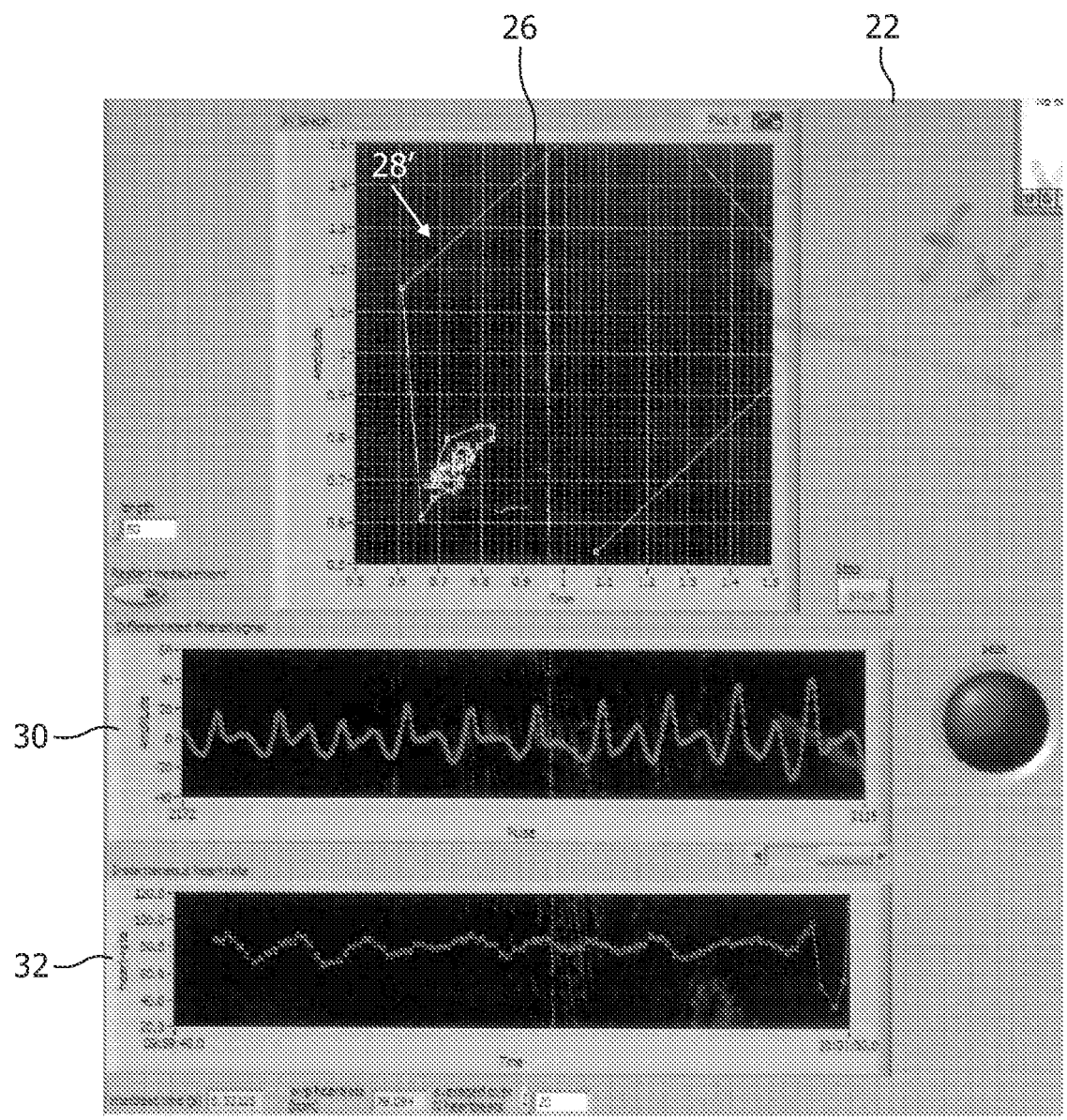

The feedback to the users 12 is in this case the ellipses 28. These constitute the output based on the measured physiological parameters of the users 12. The users 12 can view the ellipses 28 to see their current performance in the exercise that they are performing. The shape and configuration of the ellipse 28 assists the user in determining the quality of their current physiological state. For example, an opener and thinner ellipse 28 shown by the interface 22, can be taken to represent a more "coherent state" of the user, which indicates a good syncing between the user's breathing pace and heart rate. The thickness of the line of the ellipse 28, i.e. the variation in radius, is a measure for the coherence. Any break of the coherence state of the user 12, for example as the result of getting distracted or startled, results in an abrupt and immediate deviation from the ellipsoidal path. An example of such an output is shown in FIG. 6.

In this Figure, the ellipse 28' has broken away from the path previously defined by the points in the graph 26 in a swift and obvious manner. This allows fast visualization and detection, by the user, of a break in their exercise. With the ellipsoidal visualization method described above, break detection takes about one second. Fast detection is advantageous, because feedback and corrective measures, such as respiration pacing can be used much faster, leading to a speedy recovery of the coherent state. The experience of the person 12 who is trying to de-stress is greatly enhanced because of this. FIG. 6 shows the ellipse 28' in the upper graph 26, showing effect of a user being startled, on the interbeat interval. The data points jump away from the previous path of the ellipse, showing immediately that an event occurred.

The above description is detailed with respect to two users 12, but instead of two persons 12 and two ellipses 28, this method can be extended to more users, without any great adaptation of the methodology.

Figure 7:
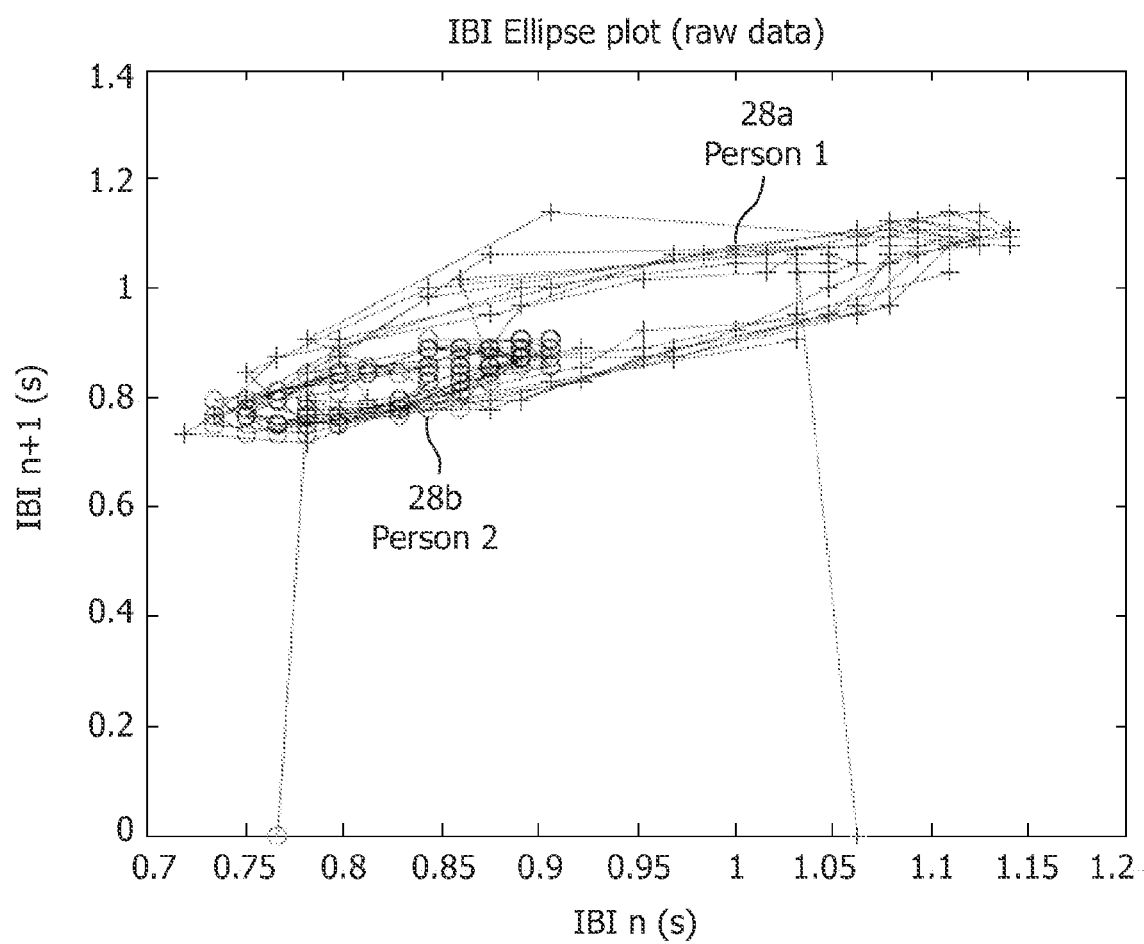
FIG. 7 is a schematic diagram showing measured physiological data for two different users.

The output of the data about the physiological parameters measured by the system 10 can be carried out in many different ways. A second embodiment will now be described, which results in the data being displayed as a three-dimensional helix. This embodiment is based on the first embodiment. In order to plot a double helix in three dimensions, the two raw data ellipses 28, as shown in FIG. 7, are captured. FIG. 7 shows the raw data IBI ellipses 28 taken from two users 12. The first user "Person 1" is represented by the data plot 28a, and the second user "Person 2" is represented by the data plot 28b. In the first embodiment, these ellipses 28 are shown to the users 12 as is, but in this second embodiment the data is further processed prior to the output to the respective users 12.

Figure 8:
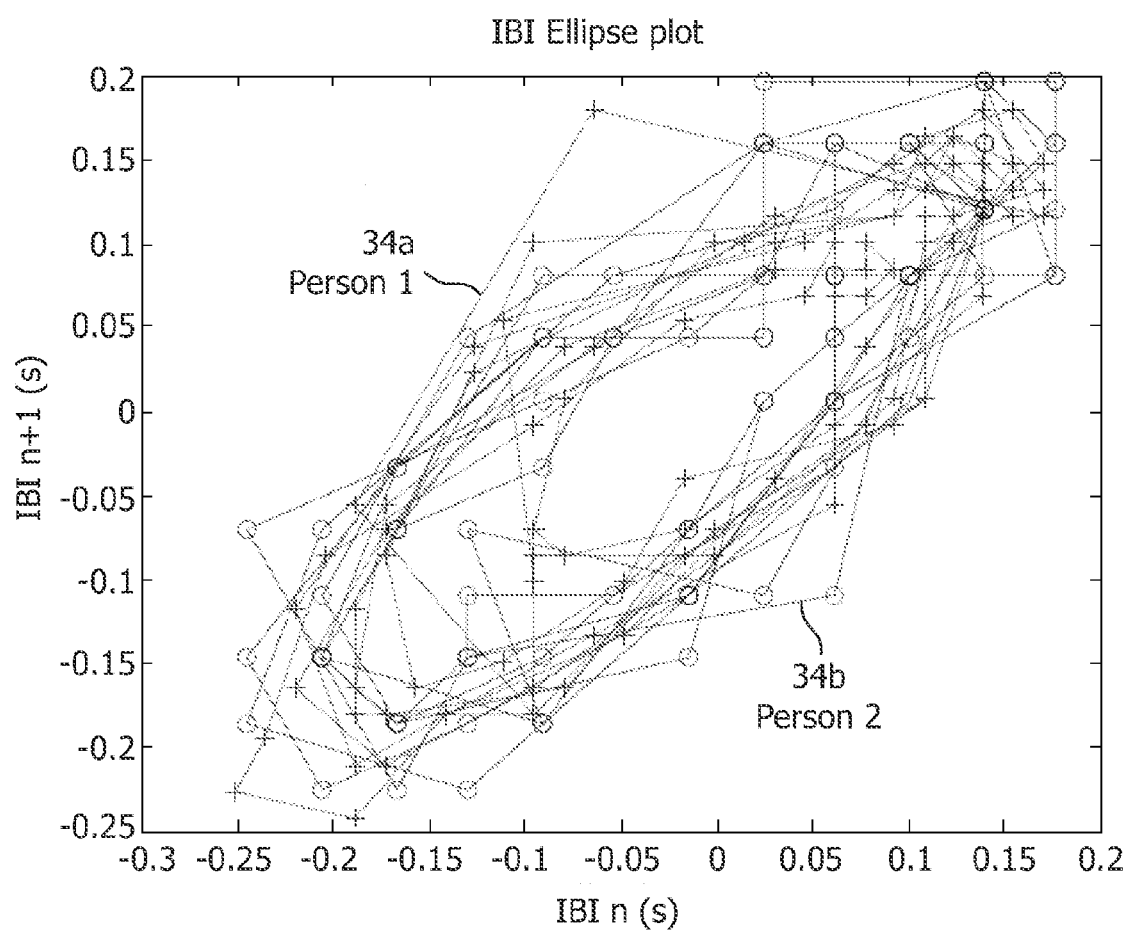
FIG. 8 is a schematic diagram showing the data of FIG. 7, following translation and scaling.

The ellipses 28 are translated to the origin by subtracting the average IBI. Subsequently they are rescaled such that they overlap. The result is shown in FIG. 8. The rescaling factor is a measure for the relative amplitudes of both persons' HRVs.

Figure 9:
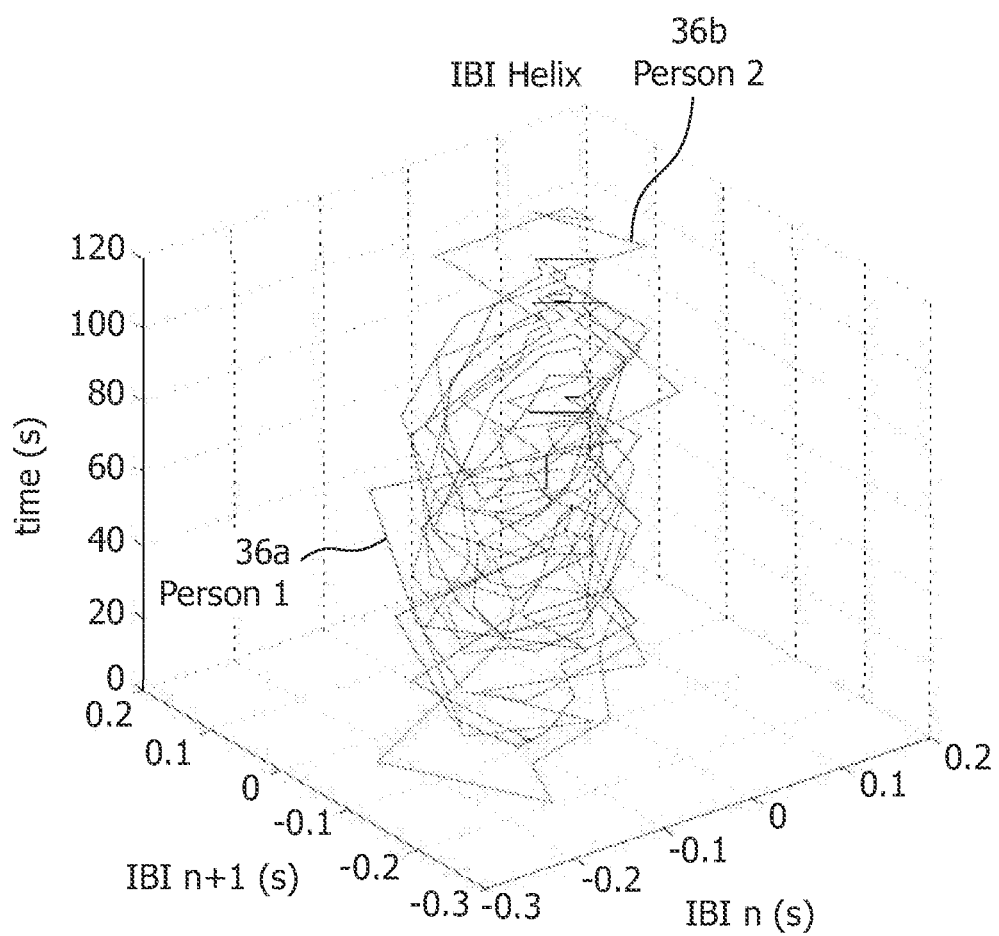
FIG. 9 is a schematic diagram showing the data of FIG. 8, following addition of a time axis.

FIG. 8 shows the translated and scaled IBI ellipses 34a and 34b for the two users Person 1 and Person 2, respectively. After the ellipses 28a and 28b are translated and rescaled, there is added a third dimension to the plot, which is time. The resulting double helix like structures 36a and 36b are shown in FIG. 9. A smoother representation is possible by proper filtering or averaging. FIG. 9 shows the double helixes 36 based on IBI data of the two users Person 1 and Person 2. The time evolution of the data points on the ellipse can be monitored more easily by using a time axis for the 3rd dimension in the plot, as shown in FIG. 9. Such a representation also conveys a sense of entanglement between the two persons. The three-dimensional helix representation allows feedback of the accurateness of the 180 phase shift in the heart rate variability.

Other representations of the data are possible. For example, in a two-dimensional (ellipse-type) plot, the last, for example ten, IBI data points could be shown using a different color in the two-dimensional plot. Other alternative ideas include the user of a changing color from the fully saturated (last data point) to the unsaturated (first data point that is still displayed) display of plots on the graphical display.

Figure 10:
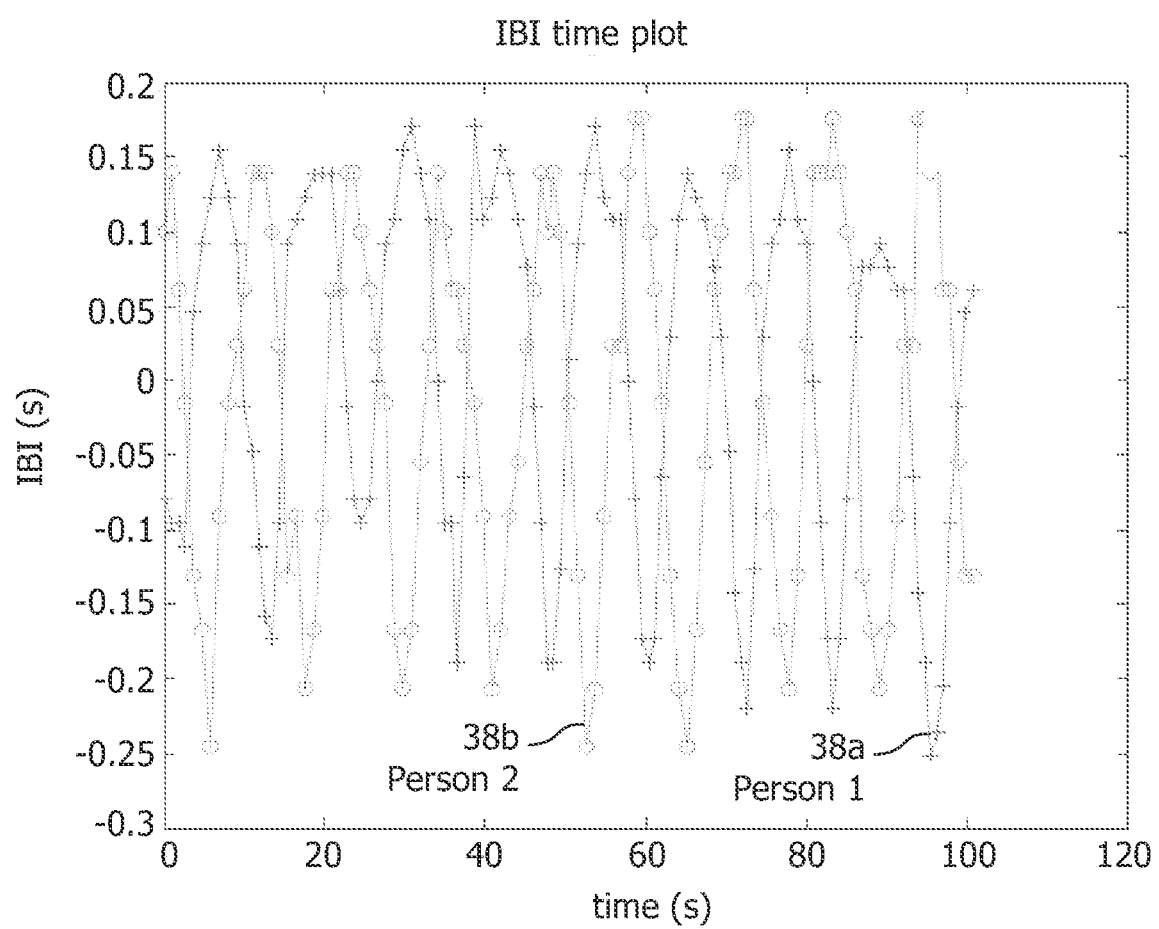
FIG. 10 is a further schematic diagram showing measured physiological data for two different users.

In a further embodiment of the system 10, the output to the users can be used in tantra. From tantra it is known that when two persons make love and breathe in anti-phase this can lead to higher ecstasy. In order to determine this phase the IBIs of both persons are plotted in time as shown in FIG. 10. In this Figure, the data plots 38a and 38b of two users 12 are shown.

The interference pattern of the two curves can be determined by adding the two curves. Subsequent squaring and summing can be performed on the addition of the two curves, which results in a number being generated as an output. The smaller this number the better the two persons breathe in antiphase (ideally this number should be zero). The idea is to provide a method to quantify the engagement into the act of the two persons. The visualization method shown in FIG. 8 allows breaks in the anti-coherence of the respiration cycle to be detected easily and soon after occurrence. Pacing aids such as colored lights dimming and intensifying may be used to facilitate entering pure anti-coherence.

This invention can be applied in the field of lifestyle and wellness. More specifically yoga training, tantra (contrary breathing) for two persons, and games in which multiple persons have to regulate their HRV in order to reach an optimal result (for example double, triple, or quadruple helix).

The system 10, as well as being used by two people who are present at the same location can also be implemented to connect together people who are spread globally. The inventive system 10 can be used to deliver an Internet based group meditation service, for example offering the pacing of the breathing rhythm or the heart rate variability. A synchronized pacer breathing pacer can facilitate the attunement of people joining in a group meditation. Being part of an attuned group can be a transformative experience. If such an attunement is offered through the Internet much larger audiences can be in tune with each other, greatly strengthening the beneficial effect.

In this embodiment, the system 10 is adapted so that a service provider offers a synchronized heart rate variability pacer or breathing pacer, onto which users can log in. A heart rate or respiration sensor 18 can be used to quantify the compliance with the pacing rhythm 16. The level of compliance is uploaded to the service provider. The purpose is to facilitate the attunement of the users 12 joining in a group meditation. The number of users 12 tuned in can be displayed.

The quality of attunement can be displayed as some kind of Gaussian curve offsetting the pacer timing. The progress towards perfect attunement can be shown by comparing the result of the present meditation session with that of previous sessions. The system 10 can therefore be used in an Internet group meditation service.

The invention claimed is:

1. A method of synchronizing a heart rate parameter of multiple users comprising:
   generating a pacing signal at a specific frequency;
   measuring a physiological parameter of each of the multiple users;
   presenting to each user an output based upon the measured physiological parameter of the respective user; and
   presenting to each user an output based upon the generated pacing signal,
   wherein a phase of the pacing signal is different for at least two of the multiple users.

2. The method according claim 1, wherein he measured physiological parameter comprises heart rate variability.

3. The method according to claim 2, wherein the step of presenting to each user an output based upon the measured physiological parameter of the respective use comprises displaying a helicoidal representation of the user's heart rate variability over time.

4. The method according to claim 1, wherein the step of generating a pacing signal at a specific frequency comprises using at least one of the measured physiological parameters as an input into the generation of the pacing signal.

5. The method according to claim 1, and further comprising presenting to a user an output based upon the measured physiological parameter of a different user.

6. The method according to claim 1, wherein the step of presenting to each user an output based upon the generated pacing signal, comprises presenting a first user with a first output, and presenting a second user with a second output, the second output out of phase with the first output.

7. The method according to claim 6, wherein the first output is substantially 180 degrees out of phase with the second output.

8. The method according to claim 6, and further comprising determining the gender of the user, wherein the first output is presented to a male user, and the second output is presented to a female user.

9. A system for synchronizing a heart rate parameter of multiple users comprising:
   a processor arranged to generate a pacing signal at a specific frequency, and, for each user;
   a sensor arranged to measure a physiological parameter of a user; and
   an output system arranged to present to the user an output based upon the measured physiological parameter of the respective user, and to present to the user an output based upon the generated pacing signal,
   wherein a phase of the pacing signal is different for at least two of the multiple users.

10. The system according to claim 9, wherein the measured physiological parameter comprises heart rate variability.

11. The system according to claim 10, wherein the output system comprises a display device arranged to display a helicoidal representation of the user's heart rate variability over time.

12. The system according to claim 9, wherein the processor is arranged, when generating a pacing signal at a specific frequency, to use at least one of the measured physiological parameters as an input into the generation of the pacing signal.

13. The system according to claim 9, wherein the output system is further arranged to present to a user an output based upon the measured physiological parameter of a different user.

14. The system according to claim 9, wherein the output system is arranged, when presenting to each user an output based upon the generated pacing signal, to present a first user with a first output, and to present a second user with a second output, the second output out of phase with the first output.

15. The system according to claim 14, wherein the first output is substantially 180 degrees out of phase with the second output.

16. The system according to claim 14, wherein the processor is arranged to determine the gender of the user, wherein the first output is presented to a male user, and the second output is presented to a female user.

* * * * *